(12) United States Patent
Joaquim Rodrigues et al.

(10) Patent No.: US 10,208,280 B2
(45) Date of Patent: Feb. 19, 2019

(54) SYSTEM AND METHOD OF PRESERVATION, STORAGE AND TRANSPORT OF BIOLOGICAL MATERIALS

(71) Applicant: INSTITUTO SUPERIOR TECNICO, Lisbon (PT)

(72) Inventors: Miguel Angelo Joaquim Rodrigues, Quinta Do Conde (PT); Vitor Manuel Geraldes Fernandes, Lisbon (PT)

(73) Assignee: INSTITUTO SUPERIOR TECNICO, Lisbon (PT)

( * ) Notice: Subject to any disclaimer, the term of this patent is extended or adjusted under 35 U.S.C. 154(b) by 64 days.

(21) Appl. No.: 15/114,715

(22) PCT Filed: Jan. 27, 2015

(86) PCT No.: PCT/IB2015/050610
§ 371 (c)(1),
(2) Date: Jul. 27, 2016

(87) PCT Pub. No.: WO2015/114516
PCT Pub. Date: Aug. 6, 2015

(65) Prior Publication Data
US 2016/0348060 A1    Dec. 1, 2016

(30) Foreign Application Priority Data

Jan. 28, 2014 (PT) .......................... 107427

(51) Int. Cl.
*C12M 1/00* (2006.01)
*C12M 3/00* (2006.01)
(Continued)

(52) U.S. Cl.
CPC .......... *C12M 45/22* (2013.01); *A01N 1/0252* (2013.01); *A01N 1/0263* (2013.01);
(Continued)

(58) Field of Classification Search
CPC ...... C12M 23/14; C12M 23/52; C12M 45/22; C12M 41/34; C12M 41/18; C12M 37/04;
(Continued)

(56) References Cited

U.S. PATENT DOCUMENTS

| 5,609,035 A | 3/1997 | Cothern et al. |
| 7,353,658 B2 | 4/2008 | Voute et al. |

(Continued)

FOREIGN PATENT DOCUMENTS

| EP | 2016356 A1 | 1/2009 |
| WO | 2011098996 A2 | 8/2011 |

OTHER PUBLICATIONS

International Search Report dated May 15, 2015 for PCT/IB2015/050610.

*Primary Examiner* — Michael L Hobbs
(74) *Attorney, Agent, or Firm* — Lucas & Mercanti, LLP

(57) ABSTRACT

A system and method for preservation, storage and transport of biological materials by the use of at least one deformable container configured with at least one inlet at one end, an outer surface greater than 80% of the total surface of the cavities of the support and a width and length sufficient for it to be placed in contact with all the heat transfer plates of the support. The support has at least two cavities delimited by the heat transfer plates, with temperature control device, side walls and at least one main front door. The system allows improvement of the heat transfer necessary for freezing and thawing large volumes of solutions containing biological materials. It also allows to considerably accelerate the heat transfer, as well as the reproducibility and scalability of the freezing and thawing process while keeping the system very compact.

25 Claims, 14 Drawing Sheets

(51) Int. Cl.
  *A01N 1/02* (2006.01)
  *C12M 1/12* (2006.01)
  *C12M 1/02* (2006.01)
  *C12M 1/34* (2006.01)

(52) U.S. Cl.
  CPC ......... *A01N 1/0273* (2013.01); *A01N 1/0289* (2013.01); *C12M 23/14* (2013.01); *C12M 23/52* (2013.01); *C12M 37/04* (2013.01); *C12M 41/18* (2013.01); *C12M 41/34* (2013.01)

(58) Field of Classification Search
  CPC .. A01N 1/0289; A01N 1/0273; A01N 1/0263; A01N 1/0252
  See application file for complete search history.

(56) References Cited

U.S. PATENT DOCUMENTS

| | | | |
|---|---|---|---|
| 2004/0006999 A1 | 1/2004 | Brown et al. | |
| 2005/0060063 A1* | 3/2005 | Reichelt | G07F 5/18 700/244 |
| 2007/0160499 A1* | 7/2007 | Mank | B04B 5/0428 422/72 |
| 2011/0258837 A1* | 10/2011 | Scannon | G05B 19/4188 29/592 |
| 2012/0305570 A1* | 12/2012 | Aprea | A01N 1/0252 220/592.02 |
| 2014/0011182 A1* | 1/2014 | Van Sickle | A01N 1/021 435/1.3 |

* cited by examiner

SYSTEM AND METHOD OF PRESERVATION, STORAGE AND TRANSPORT OF BIOLOGICAL MATERIALS

CROSS REFERENCE TO RELATED APPLICATION

This Application is a 371 of PCT/IB2015/050610 filed on Jan. 27, 2015, which claims priority of Portuguese Application No. 107427 filed Jan. 28, 2014, each of which are incorporated herein by reference.

TECHNICAL FIELD

The present application describes a system and method for preservation, storage and transport of biological materials.

STATE OF THE ART

The lifetime of biological materials dissolved or in suspension in liquid mixtures may be increased by storage at low temperature, which often entails freezing. The freezing and thawing may be applied to various biological substances, in the form of molecules, microorganisms or particles, which are typically dissolved or in suspension in aqueous mixtures.

The process of freezing and thawing is widely used in chemical, pharmaceutical and food industries, where significant amounts of intermediate or final products have to be preserved for long periods, considering the stability of sensitive substances. By increasing the lifetime of a substance, the freezing and thawing allow greater flexibility, either from the point of view of optimizing the production, for example by producing larger quantities and longer storing, or by allowing transport between plants for distribution of the production strain; or also by facilitating stock control.

In the past decades several devices and systems for freezing and thawing biological materials have been developed, such as those disclosed in documents EP2016356A1, U.S. Pat. No. 7,353,658B2, U.S. Pat. No. 5,609,035 and U.S. Pat. No. 5,609,035. However, the freezing-thawing of volumes greater than a few liters still present severe problems, especially when the process requires high levels of reproducibility under sterile conditions and in accordance with the standards of good manufacturing practice (GMP—Good Manufacturing Practices).

Mechanisms associated with degradation of sensitive substances during the process of freezing and thawing are complex and poorly understood. However, strong evidence show that homogeneous ice matrix, i.e., without significant change of composition (cryoconcentration), reduces degradation of biological proteins during the process of freezing, storage in the frozen form and thawing [1]. It is also agreed that slow freezing and thawing compromises the stability of biological substances, for example during the freezing and thawing of serum.

There is a global trend towards the implementation of systems that incorporate disposable containers configured to contain biological materials, and which may be pre-validated to operate under the strict rules imposed by regulatory agencies, thus relieving the producers from complications associated with validation of the cleaning and sterilization of the equipment.

For purposes of development and validation of freeze-thawing procedures, it is desirable for the equipment to be linearly scalable from small to large volumes, and at the same time presenting good reproducibility in all size ranges. Ideally, the system should be able to store the biological materials under sterile conditions, but with ease of operation, e.g. easy filling, transportation and discharge. Most approaches for freezing of volumes greater than few liters fall into two categories: those that use a single large container, with hundreds of liters, and those that use multiple containers of small volumes between 1 and 20 liters. Each of these technologies has advantages and limitations. For example, systems that allow freezing hundreds of liters in a single container, as disclosed in document EP1407202B1, are very practical in terms of filling, transportation and unloading. However, the reduced aspect ratio, here defined as the ratio between the heat transfer surface of the container and the volume of the filled container, imposes severe limitations to heat transfer. For example, the circulation of a diathermic fluid in the outer jacket is not sufficient to ensure rapid freezing and thawing. To some extent, this limitation has been circumvented by immersion of surfaces for heat transfer, in the form of fins and tubes, in the solution containing the biological materials to improve the heat transfer rate. However, this approach imposes complications during washing and sterilization of the equipment. Furthermore, in this configuration it is difficult to control the heat transfer during freezing and thawing, as is known to cause natural convection and cryoconcentration, which results in poor uniformity and reproducibility. The other alternative consists in dividing the total volume of biological materials for several containers of few liters. These containers can then be integrated into systems that provide conditions for freezing and thawing several containers simultaneously. This approach solves the problem of low aspect ratio, allowing for a rapid exchange of heat and an improved control of freezing and thawing, and enables the use of disposable containers. However, it has serious disadvantages regarding handling operations. By splitting the batches in many containers the number of inventory items and the number of procedures involving human operator, for assembling, filling, shipping, packaging, etc., as well as the risk of human error always associated to such operations [2], is considerably increased. Ideally, the equipment for freezing and thawing should combine the benefits of each of these approaches, i.e. ease of operation, fast and reproducible freezing and thawing, and disposal of cleaning and sterilization that is provided by the use of disposable containers. However, a system capable of providing these advantages to biological materials with volumes up to 10 $m^3$ does not yet exists.

SUMMARY

The present application describes a system of preservation, storage and transport of biological material comprising the following elements:
  a support (100) with at least two cavities (101) delimited by heat transfer plates (132), with means for temperature control, side walls (103) and at least one main front door (102);
  at least one deformable container with at least one inlet at one end, an outer surface higher than 80% of the total surface of the cavities (101) of the support (100) and a width and length sufficient for it to be placed in contact with all heat transfer plates (132) of said support (100).

In one embodiment, the deformable container used in the system for preservation, storage and transport of biological materials is a deformable container of single bag (200) or a deformable container of multiple bags (502).

In another embodiment, the deformable container of the system for preservation, storage and transport of biological materials is placed in at least two cavities (101).

In yet another embodiment, the deformable container of the system for preservation, storage and transport of biological materials supports a volume greater than 80% of the total volume of the cavities (101) of the support (100).

In one embodiment, the deformable container of the system for preservation, storage and transport of biological materials supports a volume equal to or greater than the total volume of the cavities (101) of the support (100) when these are empty.

In another embodiment, the deformable container of multiple bags (502) of the system for preservation, storage and transport of biological materials comprises expandable bags (504).

In yet another embodiment, the deformable container of the system for preservation, storage and transport of biological materials has bellows (202).

In one embodiment, the deformable container of the system for preservation, storage and transport of biological materials provides a wall made by composite film.

In another embodiment, the deformable container of the system for preservation, storage and transport of biological materials has fixing elements for connection to the support (100).

In yet another embodiment, the support (100) of the system for preservation, storage and transport of biological materials comprises a compressible insulator, sufficiently compressible to absorb the mechanical stresses caused by the expansion of the biological material due to freezing.

In one embodiment, the support (100) of the system for preservation, storage and transport of biological materials has at least one opening (129) for exchanging gases in the side walls (103) and in the doors.

In another embodiment, the support (100) of the system for preservation, storage and transport of biological materials has lower hatch (112) and upper hatch (116) in the sidewalls (103) and/or in the doors.

In yet another embodiment, the support (100) of the system for preservation, storage and transport of biological materials has at least one inspection hatch or window in the side walls (103) and/or in the doors.

In one embodiment, the support (100) of the system for preservation, storage and transport of biological materials has heat transfer plates (132) that comprise cavities (101) for circulation of a diathermic fluid.

In another embodiment, the support (100) of the system for preservation, storage and transport of biological materials has heat transfer plates that comprise cavities (101) with static mixers.

In yet another embodiment, the support (100) of the system for preservation, storage and transport of biological materials has heating means at the top of the cavities (101).

In an embodiment, the support (100) of the system for preservation, storage and transport of biological materials has heating means in regions where doors are in contact with the deformable container in order to clear the flow of the liquid phase during thawing.

In another embodiment, the doors and access means of the system of preservation, storage and transport of biological materials include sealants for hermetic sealing of the cavities (101).

The present application further describes a method of preservation, storage and transport of biological materials, comprising the following steps for freezing:

placement in a support (100) having multiple overlapped cavities (101) delimited by horizontal heat transfer plates (132) and side walls (103), a deformable container with at least one inlet for fluid exchange at one end, sufficiently long to be placed in contact with the heat transfer plates (132) of the support (100), so that at least one discharge tube (206) remains in the bottom cavity (101), and that the deformable container moves from one cavity (101) to the next by folding at the ends of the heat transfer plates;

introducing a liquid containing the biological materials inside the deformable container in order to fill it;

lowering the temperature of the heat transfer plates (132) of the support (100) keeping them below the freezing temperature of the biological materials which are contained in the deformable container.

In an embodiment, the method for preservation, storage and transport of biological materials by freezing comprises the insertion of compressible materials on top of the cavities (101) of the support (100) and/or in its side walls (103).

In another embodiment, the method for preservation, storage and transport of biological materials by freezing comprises inserting materials for thermal insulation at the top of the cavities (101) of the support (100) and/or in its side walls (103).

In yet another embodiment, the method for preservation, storage and transport of biological materials by freezing comprises introducing or removing gas in the cavities (101) of the support (100).

In an embodiment, the method for preservation, storage and transport of biological materials by freezing additionally comprises the following steps:

lowering the temperature of the plates at a speed lower than 1° C. per minute, until the temperature falls between 5 to 25° C. below the freezing temperature;

inducing nucleation by means of, for example, ultrasound, abruptly lowering the pressure inside the cavities (101) or by placing the Peltier plates at the side of the cavities (101);

keeping the temperature of the plates below the freezing temperature until the biological material is completely frozen.

The present application further describes a method of preservation, storage and transport of biological materials, comprising the following steps for thawing:

thawing the portions of the biological materials that are at the container outlet by using a heater;

thawing the portions of the biological materials that are in the volume of the deformable container that is inside the cavities (101) of the support (100) heating the heat transfer plates (132), while the thawed portion of the biological material flows out of the deformable container.

In an embodiment, the method for preservation, storage and transport of biological materials comprises introducing pressurized gas into the cavity (101) of the support (100) for thawing.

In another embodiment, the method for preservation, storage and transport of biological materials comprises removing fluid thawed by means of vacuum for its thawing.

GENERAL DESCRIPTION

The present application describes systems and methods for preservation, storage and transport of biological materials using deformable containers, which can take several forms of configuration, such as deformable containers of single bag or interconnected bags configured to contain biological materials. The technology allows the improvement of the necessary heat transfer for freezing and thawing volumes, from several tens to thousands of liters, of solutions containing biological materials, through the use of deformable containers with high aspect ratio, i.e. with an aspect ratio typically greater than 5 $m^2$ per $m^3$ of biological material, that however are installed on supports with compact heat transfer plates. This strategy allows to considerably accelerating the heat transfer, as well as the reproducibility and scalability of freezing and thawing, without compromising the ease of transport and storage.

One aspect of this technology relates to the fact that a volume of liquid, between several tens to thousands of liters, can be frozen and thawed rapidly by using a deformable container, which comprises a high aspect ratio and one compact support (100) comprising several cavities (101) delimited by overlapped heat transfer plates (132) and by side walls (103). The deformable container configured to contain biological materials, comprises at least one inlet at one end, an external surface area higher than 80% of the total surface area of the cavities (101) of the support (100), sufficient length and width so that it may stay in contact with all the heat transfer plates (132) of the support (100). The support (100) comprises overlapped cavities (101) delimited by horizontal heat transfer plates (132) with temperature control, side walls (103), and has at least one door.

Another aspect of this technology relates to a method of preservation, involving freezing, comprising the steps of:
  placement of at least one deformable container in support (100), having at least two overlapped cavities (101) delimited by horizontal heat transfer plates (132) and side walls (103);
  introduction of biological materials inside the deformable container, which may be partially or completely full;
  temperature reduction of the heat transfer plates (132) of the support (100) keeping them below the freezing temperature of the biological materials that are contained in the deformable container.

Another aspect of the technology relates to the method for preservation, involving thawing, comprising the steps of:
  thawing the biological materials portions that are at the outlet of the deformable container using a heater;
  thawing the biological materials portions that are in the volume of the deformable container that is outside the cavity (101) of the support (100) using a heater;
  thawing the biological materials portions that are in the volume of the deformable container that is inside the cavities (101) of the support (100), by heating the heat transfer plates (132) while the portion of thawed biological material flows out of the deformable container.

The heater used in the first step of the above method may be integrated in the system, or any external heating source may be used, such as an electrical resistance, a dryer or other source of external heating assumed to be sufficiently effective.

The deformable container may have several forms of configuration, such as deformable containers of single bag (200) and deformable containers of multiple interconnected bags (502), configured to contain biological materials, with at least one inlet for fluid exchange at one end but with sufficient length to be placed in contact with the heat transfer plates (132) of the support (100), so that at least one inlet of the deformable container stays at the bottom cavity (101), and that the deformable container passes from one cavity (101) to the next by folding the said deformable container at the ends of the heat transfer plates (132). Thus, said deformable container has part of its volume distributed by the cavities (101) of the support (100), and another part of the volume is distributed out of the cavities (101) of the support (100).

BRIEF DESCRIPTION OF THE DRAWINGS

For an easier understanding of the invention the attached figures are joined, which represent preferred embodiments of the invention that, however, are not meant to limit the object of the present application.

104—main rear door
105—electrical connection;
106—diathermic fluid tube;
118—base;
126—cavity compressible isolator;
150—electrical resistance of the door;
502—deformable container of multiple bags;
504—expandable bags;
506—flexible interconnection tube;
510—feeding tube;
512—posterior outlet tube;
528—recess.

Figure 12:
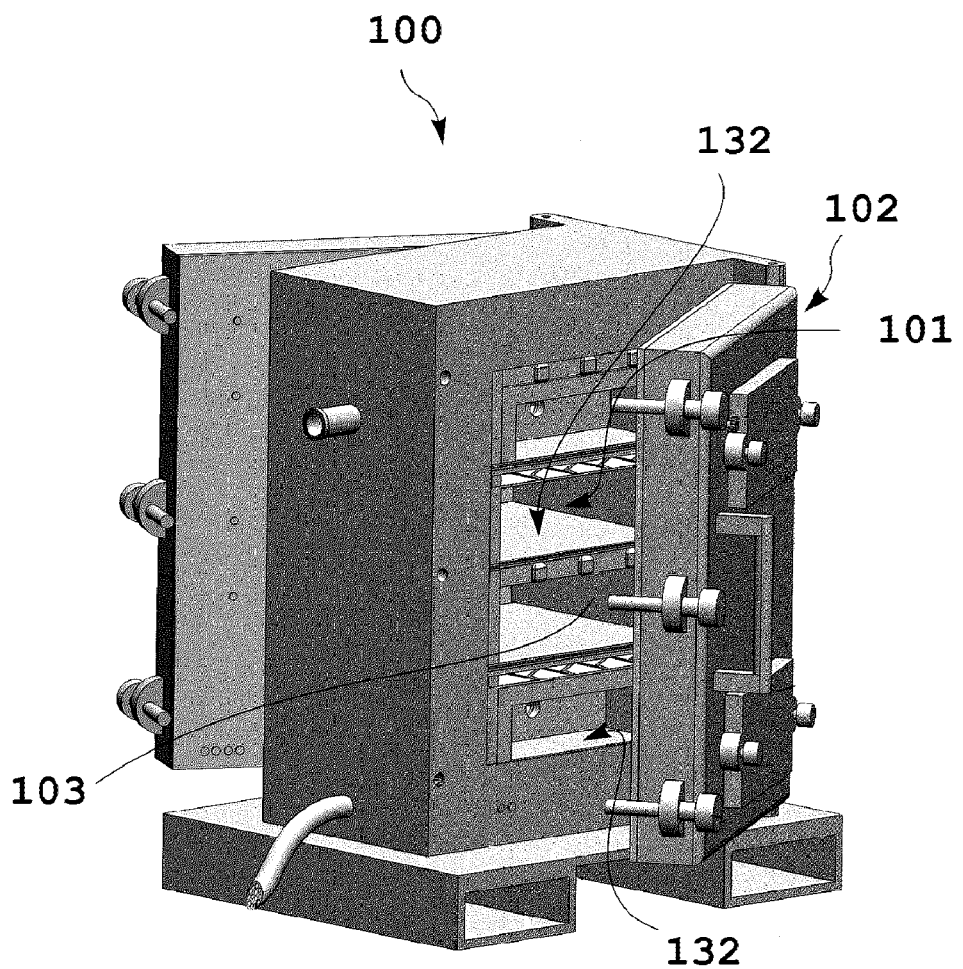

FIG. 12 schematically illustrates a front view perspective of the support, with the two main doors partially open, wherein the reference numerals indicate:
100—support;
101—cavity;
102—main front door;
103—side walls;
132—heat transfer plates.

DESCRIPTION OF EMBODIMENTS

The present application describes systems and methods for freezing, thawing, storing or transporting biological materials that include supports (100) with a plurality of overlapped cavities (101), delimited by horizontal heat transfer plates (132) supported by side walls (103) and deformable containers configured to receive biological materials.

In an embodiment, which is represented in FIGS. 1 to 11, which are not intended to limit the object of the present application, is shown a system for preserving, by processes of freezing and thawing, storage and transport of biological materials using deformable containers configured to contain biological materials. This system comprises a support (100) and a sterile deformable container, one example being the deformable container in form of a bag, configured to contain biological materials. The deformable container may adopt various forms of configuration. These include the simpler configuration of deformable container of single bag (200) and the most complex configuration of deformable container of interconnected multiple bags (502).

The support (100) comprises several cavities (101) delimited by overlapped heat transfer plates (132) and side walls (103). This configuration allows the system to be very compact, taking into consideration the outer surface of the system and the total volume of biological material that may be contained therein; this being very convenient for storage and transportation. The support (100) may have at least one main front door (102) and at least one main rear door (104). These doors can be hermetically closed for example by means of a mechanical connection, preferably by means of screws (125), rails, magnets or other means deemed possible to connect with the orifices (120) in the casing (124). Each door contains a door sealant (160) prepared as for example polytetrafluoroethylene (PTFE) or silicone, which allows to make the sealing when the door is closed. Although not shown in the figures, the main door screws (122) may have springs to ensure that the doors remain tightly closed, even when the temperature decreases and the mechanical structure of the device contracts. In the particular embodiment shown in any of FIGS. 1 to 8, the main front door (102) has two hatches, the lower hatch (112) and the upper hatch (116) to provide access to the loading and unloading tubes of the flexible container. Both hatches, lower hatch (112) and upper hatch (116) may be tightly closed for example by means of mechanical coupling, preferably by means of screws (125), rails, magnets or other means deemed possible. These two hatches, lower hatch (112) and upper hatch (116) may be removed during the filling or discharge operation, as explained later. The support (100) has at least two cavities (101), being presented in the enclosed figures one embodiment with four cavities (101) delimited by side walls (103) and heat transfer plates (132). In the example presented in the figures, there are four cavities (101) only for illustration purposes, as the support (100) may have a plurality of cavities (101). The system may further be assembled to have partitions in the same cavity (101) to facilitate storage and organization of biological products. If the number of cavities (101) is even, the two hatches, lower hatch (112) and upper hatch (116) are for example placed on the main front door (102). If the number of cavities (101) is odd, the upper hatch (116) may for instance be placed in the main rear door (104). Each main door, either the main front door (102) or main rear door (104), may have an air release valve (130) that is used to control the air intake, as discussed further below.

Figure 4:
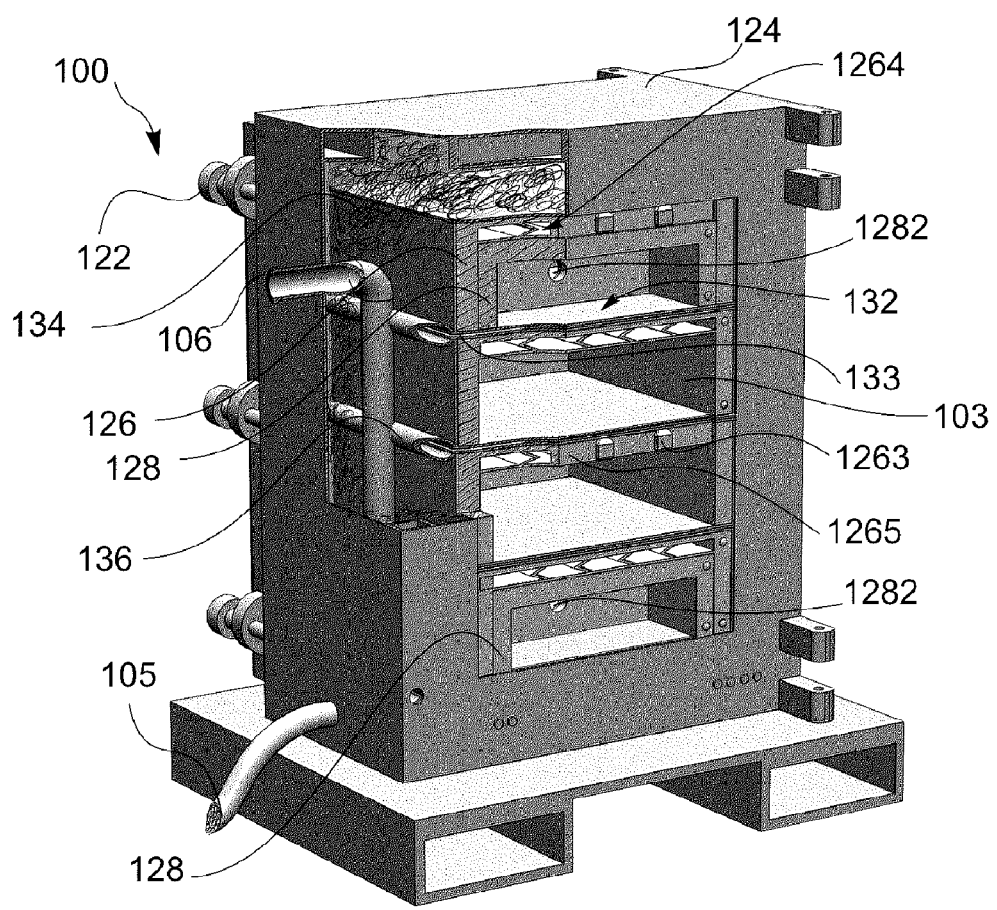
FIG. 4 schematically illustrates a perspective view of the support, partially cut, without the main front door, wherein the reference numerals indicate:
100—support;
103—side walls;
105—electrical connection;
106—diathermic fluid tube;
122—main door screws;
124—casing;
126—cavity compressible isolator;
128—support device of the container;
132—heat transfer plates;
133—feeding channels;
134—light and thermally insulating material;
136—distributing tubes;
1263—guides;
1264—consecutive cavities;
1265—protection wall;
1282—posterior orifice.

The system may be assembled over a base (118) to facilitate handling, for example by a forklift truck. The support (100) may also comprise an electrical connection (105) that connects to an electrical control unit, which does not appear in any of the figures. The heat transfer plates (132) with an essentially rectangular shape comprises cavities (101), i.e. internal channels in which a diathermic fluid can circulate that in this example enters through the diathermic fluid tube (106). In this case, this diathermic fluid tube (106) distributes the diathermic fluid through the various heat transfer plates (132), as illustrated in FIG. 4. Each cavity (101) may comprise a thermal insulator and a compressible material. In this embodiment, a cavity compressible insulator (126) is illustrated, which performs both functions. First, this component prevents heat transfer between two adjacent cavities (101) and, secondly, this component is sufficiently compressible to accommodate the increase in volume that occurs when the product freezes. The cavity compressible insulator (126) is preferably reversibly removable to facilitate cleaning of the cavities (101) of the preservation apparatus. The interior of the support (100) is shown schematically in detail in FIG. 4. The space between the casing (124) and the outer walls of the cavities (101) may comprise a thermally insulating lightweight material (134) such as polyurethane foam, expanded polystyrene, glass fibre, cork or rock wool. This isolation may be useful to minimize temperature fluctuations of the apparatus during transport and storage.

Figure 1:
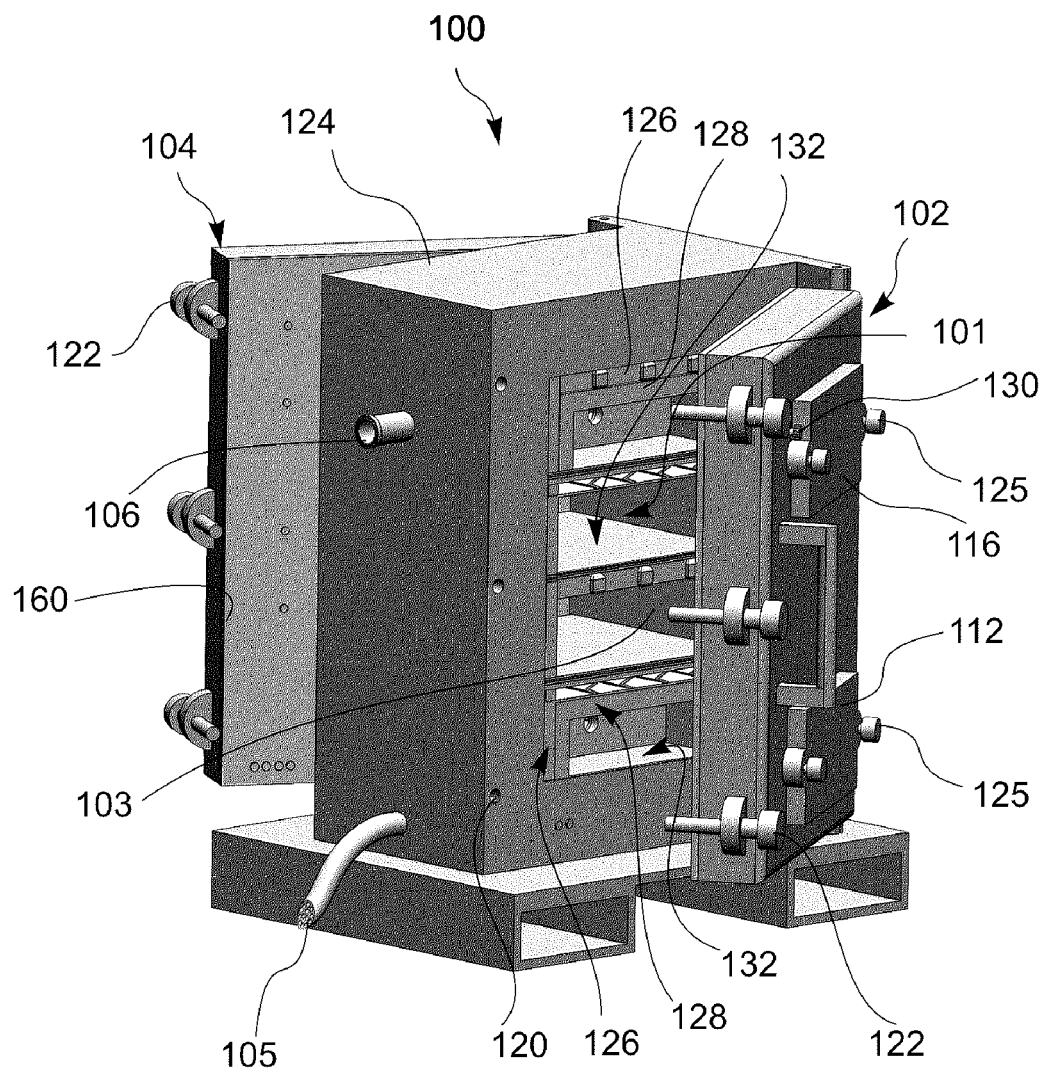
FIG. 1 schematically illustrates a front view perspective of the support, with both main doors partially open, wherein the reference numerals indicate:
100—support;
101—cavity;
102—main front door;
103—side walls;
104—main rear door;
105—electrical connection;
106—diathermic fluid tube;
112—lower hatch;
116—upper hatch;
120—orifices;
122—main door screws;
124—casing;
125—screws;
126—cavity compressible isolator;
128—support device of the container;
130—air release valve;
132—heat transfer plates;
160—door sealant.
Figure 2:
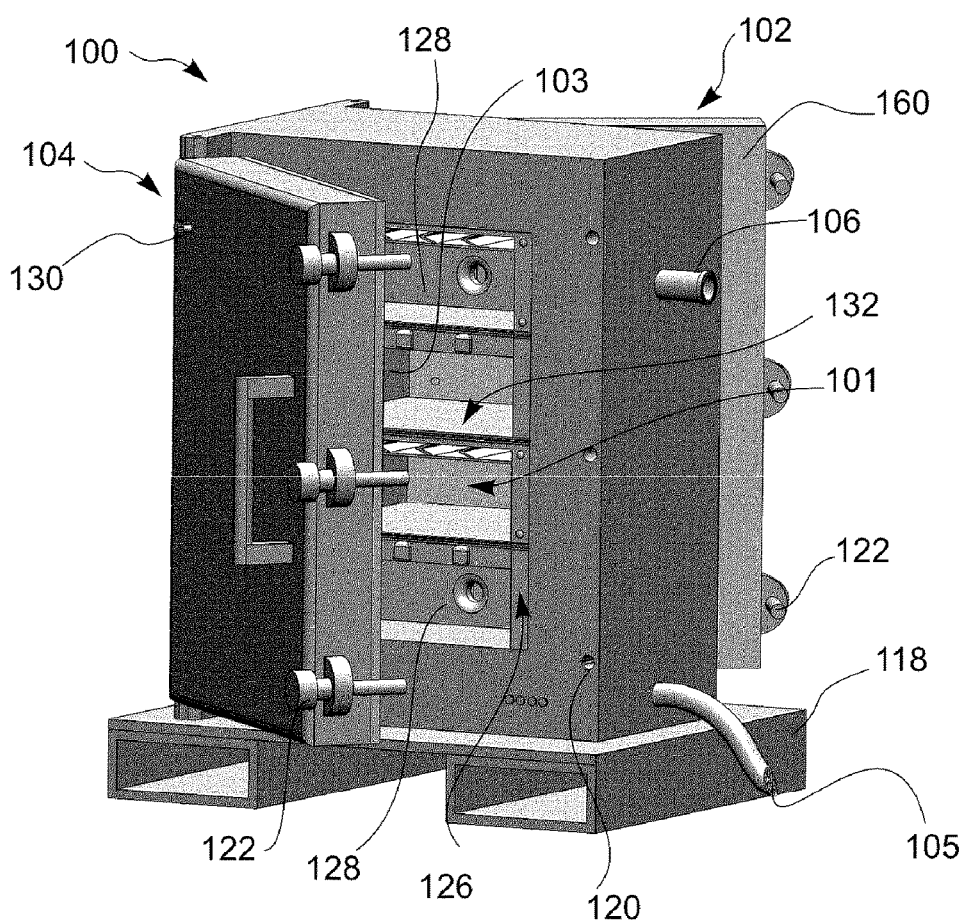
FIG. 2 schematically illustrates a rear view perspective of the support, with both main doors partially open, wherein the reference numerals indicate:
100—support;
101—cavity;
102—main front door;
103—side walls;
104—main rear door;
105—electrical connection;
106—diathermic fluid tube;
118—base;
120—orifices;
122—main door screws;
126—cavity compressible isolator;
128—support device of the container;
130—air release valve;
132—heat transfer plates;
160—door sealant.
Figure 3:
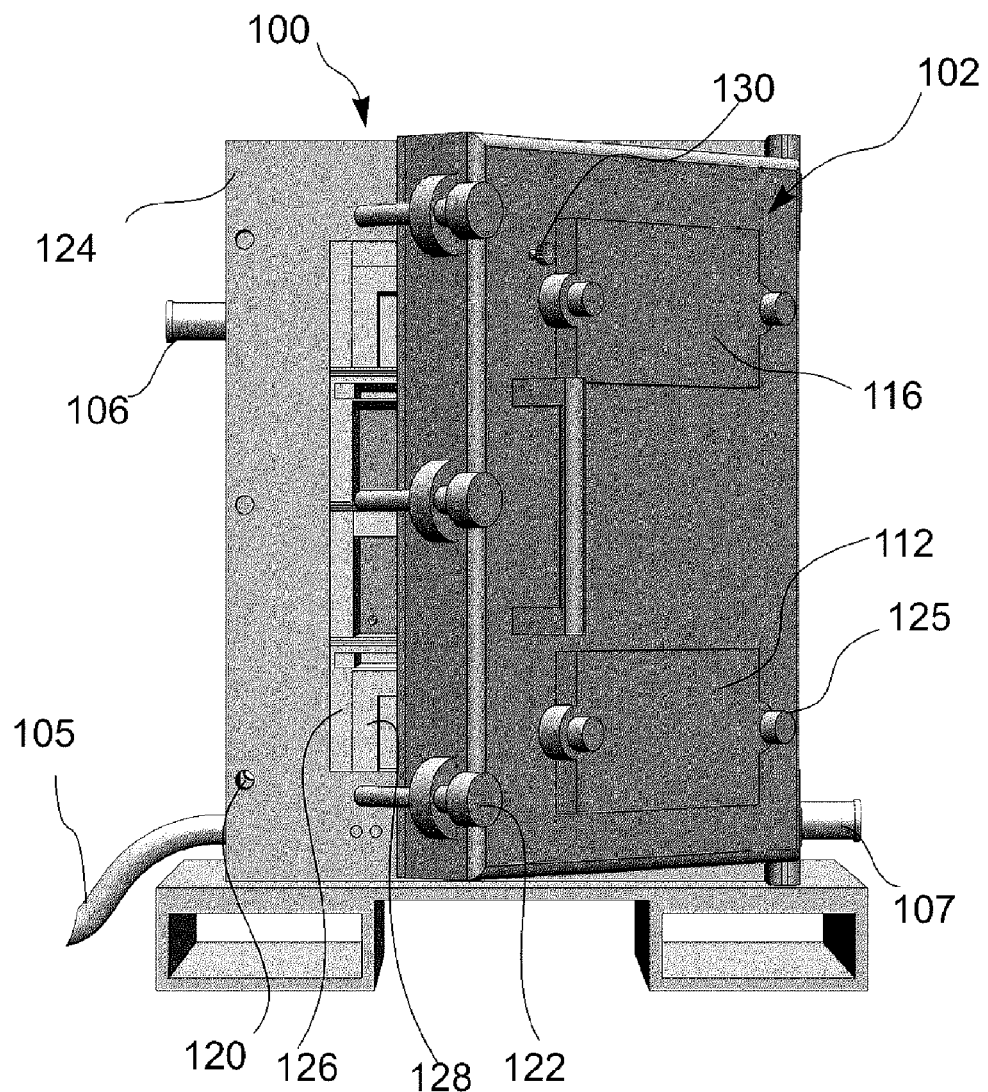
FIG. 3 schematically illustrates a front view of the support with the main front door (102) partially open, wherein the reference numerals indicate:
100—support;
102—main front door;
105—electrical connection;
106—diathermic fluid tube;
107—outlet tube;
112—lower hatch;
116—upper hatch;
120—orifices;
122—main door screws;
124—casing;
125—screws;
126—cavity compressible isolator;
128—support device of the container;
130—air release valve.
Figure 5A:
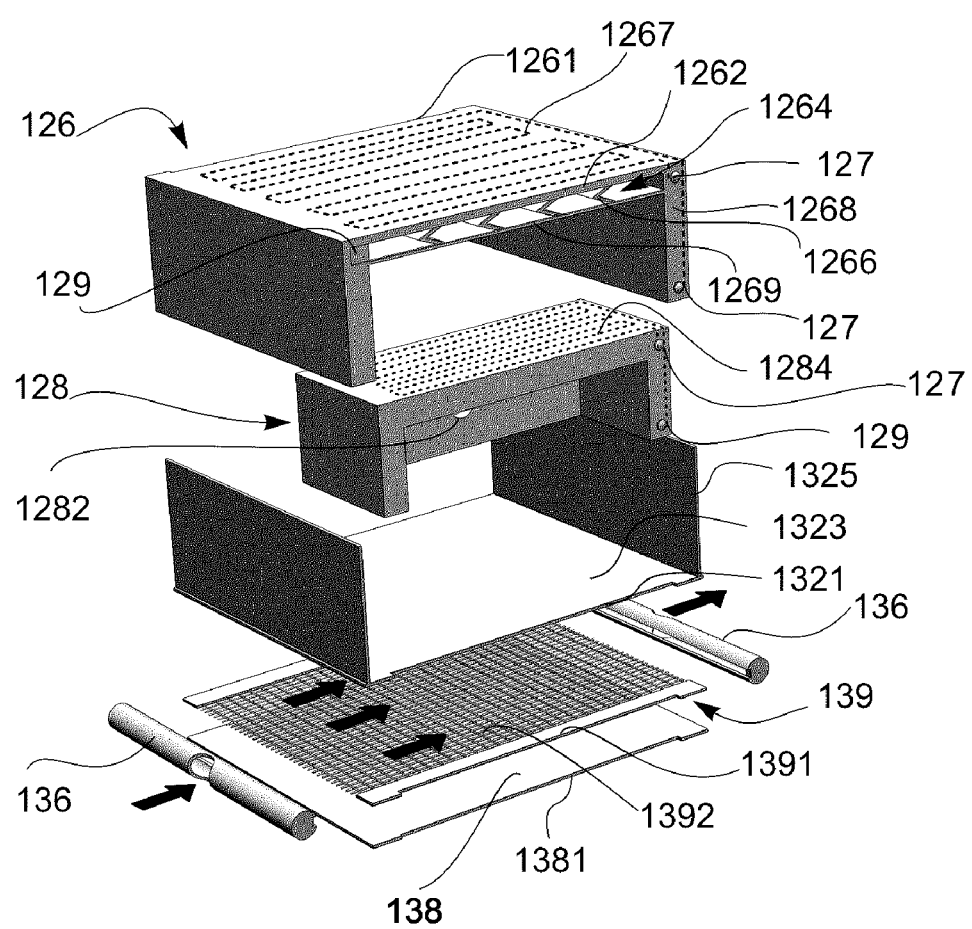
FIG. 5a illustrates an exploded perspective view of a single set of a support plate, and also the electrical parts incorporated, wherein the reference numerals indicate:
126—cavity compressible isolator;
127—electrical connections;
128—support device of the container;
129—opening;
136—distributing tubes;
138—bottom sheet;
139—metallic mesh spacer;
1261—clearance;
1262—top insulating layer;
1264—consecutive cavities;
1266—flexible side layers;
1267—electrical resistance;
1268—vertical sidewalls;
1269—flexible layer;
1282—posterior orifice;
1284—electrical resistance of the support device of the container;
1321—opening;
1323—heat transfer plate;
1325—metal sidewalls;
1381—opening;
1391—opening;
1392—metallic mesh.
Figure 5B:
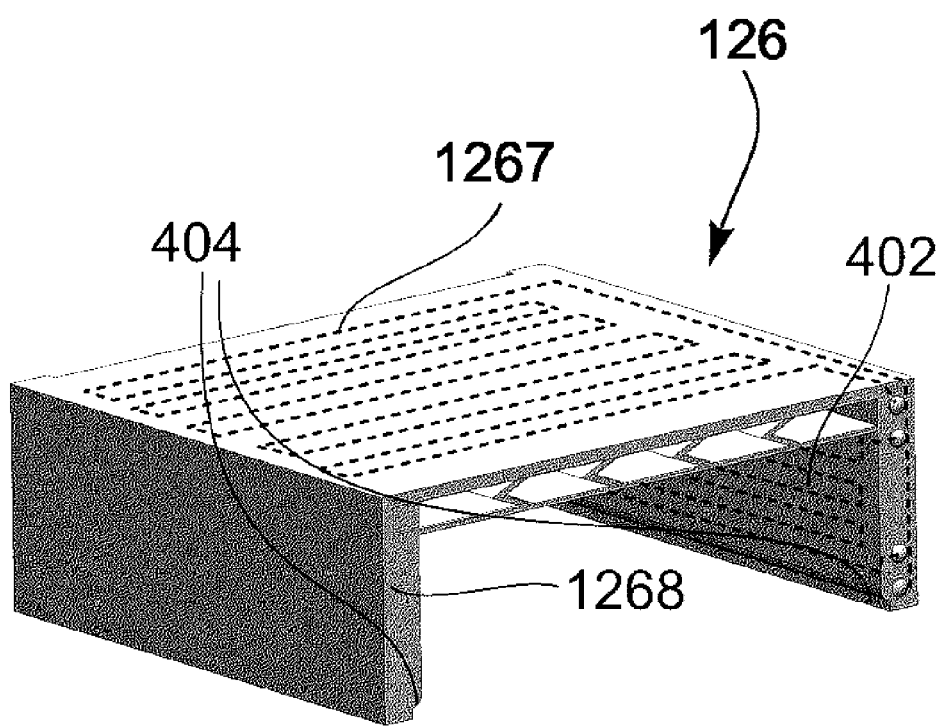
FIG. 5b illustrates one embodiment of a cavity compressible insulator, wherein the reference numerals indicate:
126—cavity compressible isolator;
402—electrical resistance of the insulator;
404—notched margin;
1267—electrical resistance;
1268—vertical sidewalls.

The cavity compressible insulator (126) may display internal consecutive cavities (1264), which are capable of deforming reversibly, when the biological material within the cavity (101) starts to expand during freezing. Internal consecutive cavities (1264) start on the open side of the cavity compressible insulator (126) and ends in the protection wall (1265). As illustrated in FIG. 4, the diathermic fluid enters through the diathermic fluid tube (106) and is then distributed by the distributor tubes (136) to the heat transfer plates (132), and is then discharged by the outlet tube (107) that is shown in FIG. 3. The distributor tubes (136) distribute uniformly the diathermic fluid through the feeding channels (133) that are inside the heat transfer plates (132). The construction details of the elements comprising a single cavity (101) and a heat transfer plate (132) of the freeze-thawing apparatus can be seen more clearly in FIG. 5a, where an exploded view of the basic elements involved is shown. In this case, the height of the cavity (101) should preferably be between 5 cm and 25 cm. The support device of the deformable container (128) is only present in the lower and cavities (101) of the support (100). The cavity compressible insulator (126) is illustrated in FIG. 5a, with the schematic representation of a heater, which may be optional, through the assembling of an electrical resistance (1267), and the electrical connections (127).

The consecutive cavities (1264) may comprise flexible side layers (1266), a flexible layer (1269) and a top insulating layer (1262). The cavity compressible insulator (126) is preferably made of a single material, which must be sufficiently compressible to be deformed when the aqueous solution containing the biological material expands due to freezing. The material of the container may be a flexible polymer with a glass transition temperature below the minimum temperature the diathermic fluid reaches during the freezing process. The cavity compressible insulator (126) may, however, also be made by combining different materials, for example, a thermal insulation material and a compressible material juxtaposed. A small opening (129) ensures the air contained in the consecutive cavities (1264) escapes freely through the channels (142) notched in the main doors, main front door (102) and main rear door (104), when the air or gas contained in the consecutive cavities (1264) is compressed by the expansion of the ice during the freezing process. The cavity compressible insulator (126) may introduce, for example, another alternative configuration shown in FIG. 5b. In this alternative configuration there is an additional lateral heater consisting, for example, an electric resistance of the insulator (402) in both vertical side walls (1268). The vertical side walls (1268) have a notched edge (404). As also shown in FIG. 5a, the diathermic fluid circulates in the feeding channels (133) of the heat transfer plate (1323) through a static mixer, which in this example comprises a metallic mesh spacer (139) that connects itself to the heat transfer plates (1323) and the bottom sheet (138).

Figure 5C:
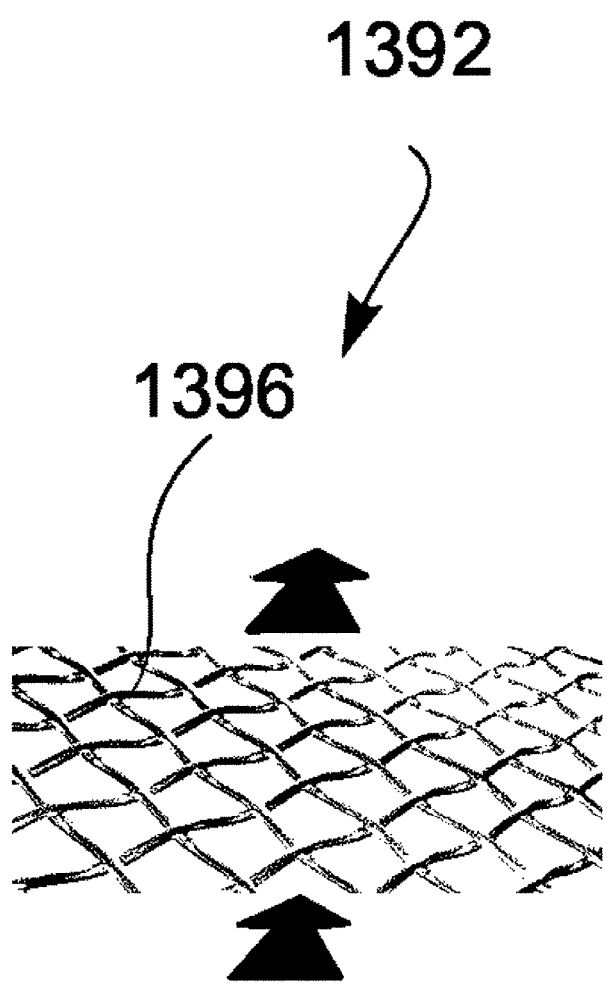
FIG. 5c illustrates one embodiment of the metallic mesh, wherein the reference numerals indicate:
1392—metallic mesh.
1396—metallic filaments.

To ensure good mechanical stability of the set of heat transfer plate (132) and to prevent deformation of the heat transfer plate (1323) and bottom sheet (138), under the pressure of the diathermic fluid, the heat transfer plate (1323) and the bottom sheet (138) are preferably connected to the metallic mesh (1392) by welding or internal braze. As is well known to one skilled in the art, the process of welding or internal braze connects the heat transfer plate (1323) and the bottom sheet (138) and the metallic mesh (1392) by means of a thin layer of secondary metal, such as nickel or metallic alloy with a melting point lower than that of the metal of the involved components. Instead of welding or internal braze, one can also connect the heat transfer plate (1323) to the bottom sheet (138) by means of mechanical bonds evenly distributed. The metallic mesh (1392) in this case has a dual function. First, it acts as a turbulence promoter, which contributes to increase the heat transfer coefficient at the diathermic fluid/plate interface. This function is particularly important to accelerate the thawing of the frozen product, because the heat transfer in this step is strongly limited by heat transfer resistance between the diathermic fluid and the inner interface of the heat transfer plate (1323). On the other hand, as already mentioned, the metallic mesh (1392) acts as a structural means to keep the heat transfer plates (1323) and the bottom sheet (138) well connected by welding or internal braze or even by mechanical bond, to avoid deformation. The distributor tubes (136) are connected to the heat transfer plates (1323) and the bottom sheet (138), preferably by welding or braze. The metallic side walls (1325) are welded to the heat transfer plate (1323) and bottom sheet (138) of the adjacent heat transfer plate, and have the function of providing mechanical support for the stacking of heat transfer plates (132) and to confine the cavity compressible insulator (126). The small opening (1381) has a preferred dimension comprised between 1 mm and 10 mm and serves to pass the biological material through the deformable container. Two juxtaposed layers of parallel metallic filaments (1396) as shown in FIG. 5a preferably constitute the metallic mesh (1392). The layer of metallic filaments (1396) in contact with the heat transfer plate (1323) should be preferably oriented perpendicular to the direction of the diathermic fluid flow, to maximize the heat transfer coefficient between the diathermic fluid and the interface of the deformable container. Alternatively, for example, another metallic mesh configuration (1392) that it is comprised of two interwoven layers of parallel metallic filaments (1396) may be used, as represented in FIG. 5c. To ensure a uniform distribution of the diathermic fluid within the feed channel (133), the parallel metallic filaments (1396) should make, preferably, an acute angle with the main flow direction indicated by arrows in FIG. 5c. The heat transfer plate (1323) can be smooth, as shown in FIG. 5a, but in an alternative embodiment, may have a notched matrix of interconnected channels or corrugations, with smooth edges to prevent damage to the walls of the deformable container. These matrixes of channels or corrugations has the important function of facilitating the fluid flow during the thawing process and, at the same time, increase the overall heat transfer coefficient during the same process. The depth of these channels or corrugations is less than 5 mm and even more preferably should be less than 2 mm.

Figure 6:
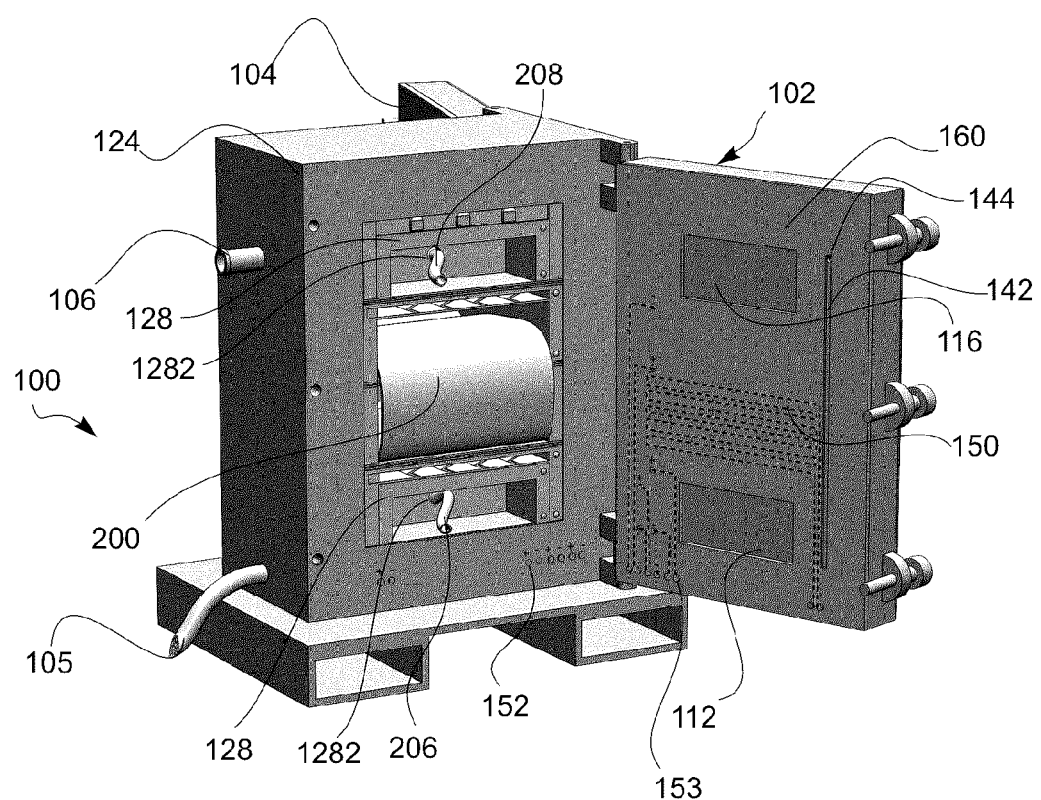
FIG. 6 illustrates a schematic front perspective view of the system of preservation, exhibiting the electrical components of the support with the two main doors partially open and with the deformable container assembled in zigzag pattern, wherein the reference numerals indicate:
100—support;
102—main front door;
104—main rear door;
105—electrical connection;
106—diathermic fluid tube;
112—lower hatch;
116—upper hatch;
124—casing;
128—support device of the container;
142—channels;
144—gas orifices;
150—electrical resistance of the door;
152—male connector;
153—female connector;
160—door sealant;
200—deformable container of single bag;
206—discharge tube;
208—inlet tube;
1282—posterior orifice.
Figure 7:
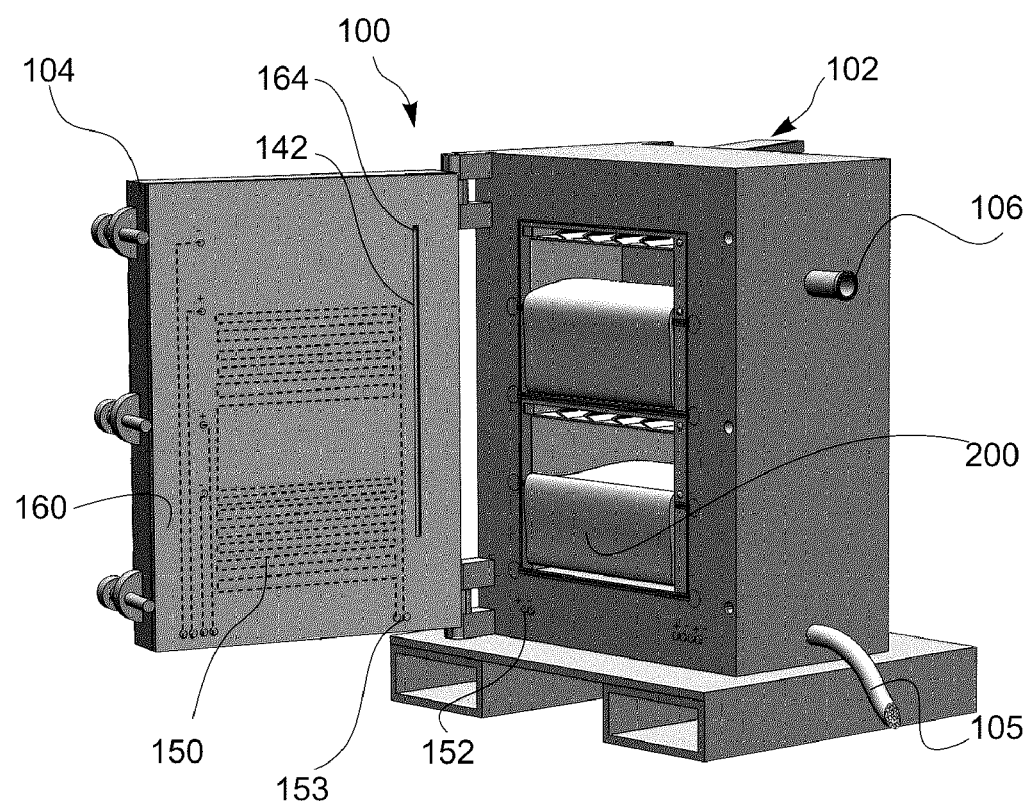
FIG. 7 schematically illustrates a rear perspective view of the system exhibiting the electrical components of the support, with the two main doors partially opened and with the deformable container assembled, wherein the reference numerals indicate:
100—support;
102—main front door;
104—main rear door;
105—electrical connection;
106—diathermic fluid tube;
142—channels;
150—electrical resistance of the door;
152—male connector;
153—female connector;
160—door sealant;
164—air orifices;
200—deformable container of single bag.
Figure 8:
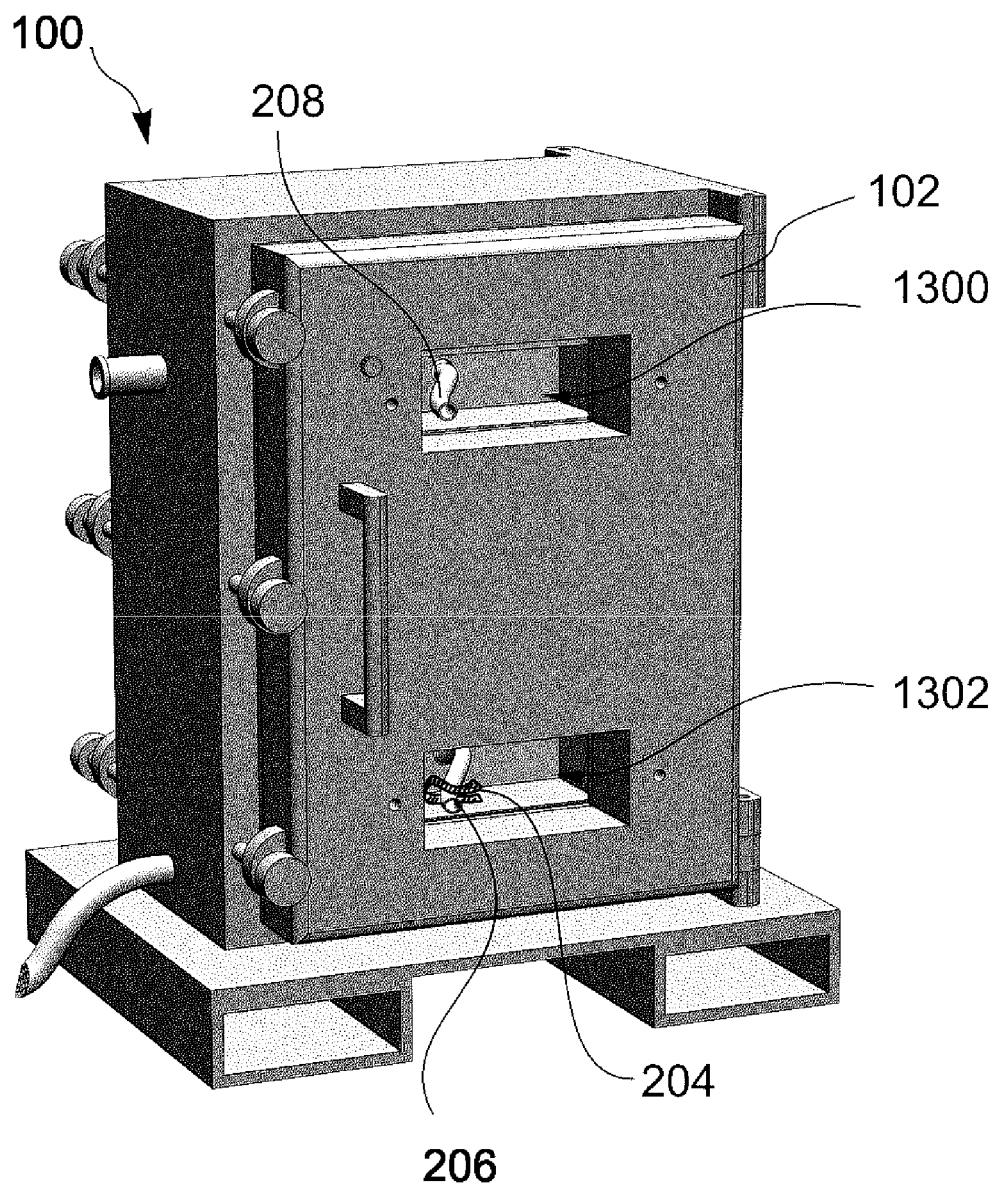
FIG. 8 schematically illustrates a front perspective view of the system, in the filling or unloading position, with the two main doors fully closed, the two hatches removed and with the deformable container assembled, wherein the reference numerals indicate:
100—support;
102—main front door;
204—clamp;
206—discharge tube;
208—inlet tube;
1300—upper opening;
1302—lower opening.
Figure 9:
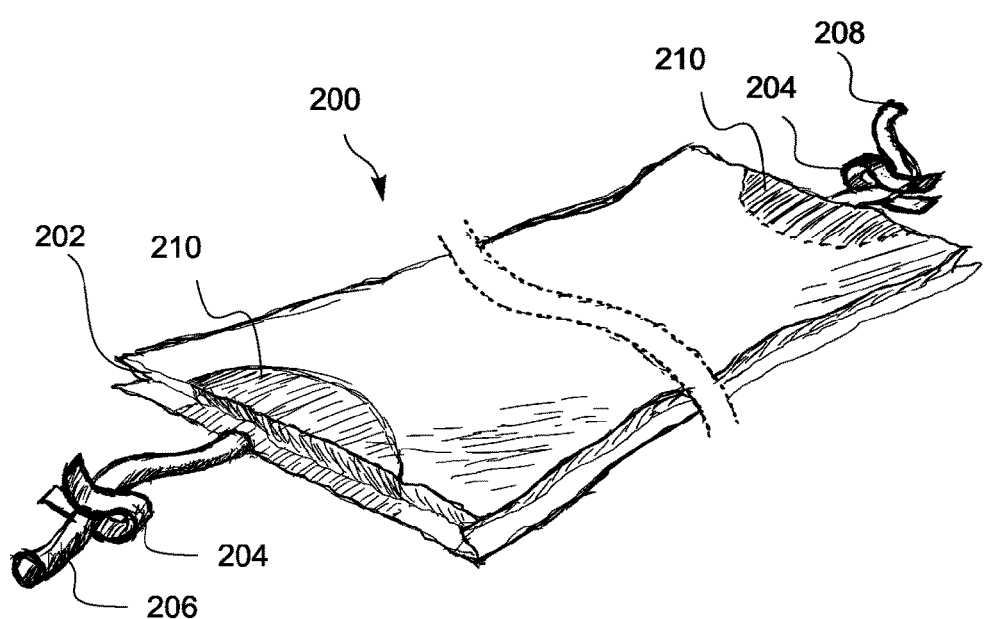
FIG. 9 schematically illustrates a perspective view of one embodiment of a deformable container of single bag with the respective reinforcing regions, wherein the reference numerals indicate:
200—deformable container of single bag;
202—bellows;
204—clamp;
206—discharge tube;
208—inlet tube;
210—reinforcing region.
Figure 10:
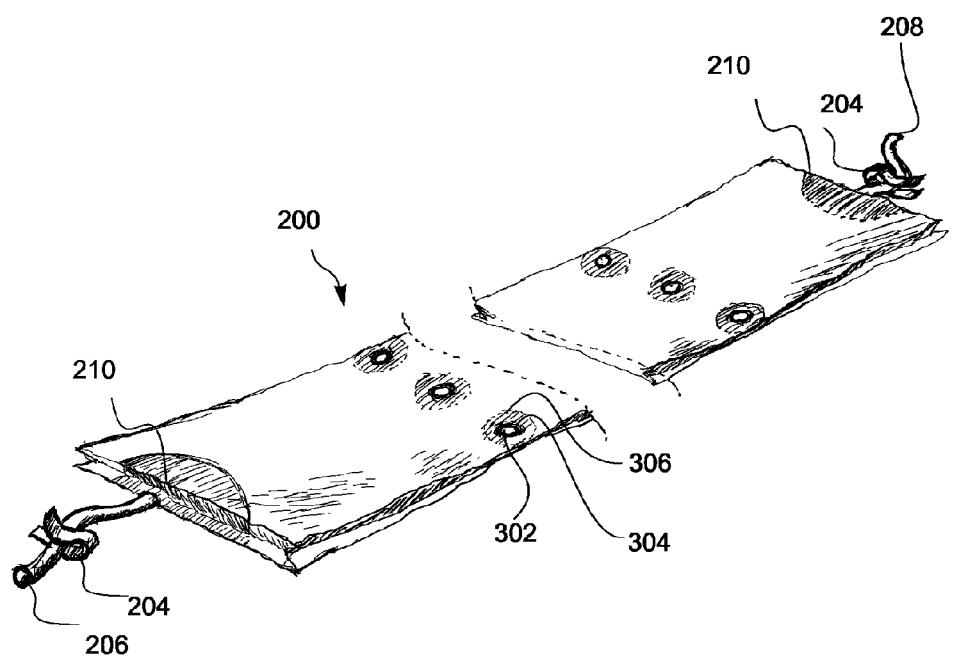
FIG. 10 schematically illustrates a perspective view of one embodiment of the deformable container, wherein the reference numerals indicate:
200—deformable container of single bag;
204—clamp;
206—discharge tube;
208—inlet tube;
210—reinforcing region;
302—fixing holes;
304—circular metallic device;
306—reinforcing layer.

The particular embodiment of the system comprised of a support (100) and a deformable container is illustrated in FIGS. 6 to 8. The deformable container is schematically represented in FIG. 9. The deformable container has an outer surface and preferably more than 80% of the total area of the cavities (101) of the support (100), and should have a sufficient width and length so that it can be placed in contact with all the heat transfer plates (1323) of the support (100). Thus, it is ensured that a container with high aspect ratio, preferably greater than 5 m$^2$ of heat transfer area per m$^3$ of volume of biological material, capable of high heat transfer rates, may be heated or cooled in a compact system. In this framework, the deformable container should preferably be capable of supporting a volume of more than 80% of the total volume of the cavities (101) of the support (100). The deformable container, outside the support (100), may support up to a volume equal to or greater than the total volume of the cavities (101) of the support (100), when empty, and when assembled to the support (100), the volume contained within the deformable container is limited to the internal volume of the support (100).

For assembling the deformable container inside the support (100), the discharge tube (206) is inserted first in the posterior orifice (1282) of the support device of the lower container (128). Then the deformable container follows a zigzag pattern configuration, passing from a cavity (101) to the next, until it reaches the support device of the deformable container (128) in the upper cavity (101). The inlet tube (208) of the deformable container is inserted in the posterior orifice (1282). The deformable container passes from a cavity (101) to the next by a clearance between the closed front doors and the heat transfer plate (132) and the cavity compressible insulator (126). As illustrated in FIG. 5a, the cavity compressible insulator (126) has a small clearance (1261), and the heat transfer plate (132) has small openings (1321, 1391 and 1381). The deformable container, illustrated in FIG. 9, is made of a flexible film, made of a simple or composite polymeric material. Preferably, the deformable container is initially under vacuum and may comprise peripheral pleats or bellows (202), to allow its expansion when filled with liquid. The number of peripheral pleats or bellows (202) should preferably be sufficient for the liquid to fill substantially the volume of the cavities (101) when the deformable container is filled. The width of the deformable container is preferably approximately equal to the clear width of the cavities (101). The length of the deformable container should be sufficient for it to fit appropriately in all cavities (101). Examples of deformable containers illustrated in FIGS. 6-9 show a liquid inlet at one end and a liquid outlet at the other end. However, the system operates according to the principles now described even though the deformable container has only one opening for liquid exchange. In this case, the deformable container is assembled on the support (100) as in the cases already exemplified, with the exception of the installation of the opening that serves as inlet, named inlet tube (208). In this case the single opening (129) of the deformable container for fluid exchange is installed in the cavity (101) of the support (100) that is at a lower height; being the deformable container filled and discharged through this opening (129) that serves therefore for fluid inlet and outlet.

To increase the speed of freezing and thawing, the thickness of the film constituting the wall of the deformable container is preferably less than 500 µm. To increase mechanical integrity of the container, an additional layer of reinforcing film may be placed on the reinforcing region (210) that is in contact with the posterior orifices (1282).

In another embodiment, the deformable container may have fixing holes (302) to be secured to respective attachment points on the borders of the plates of the support (100) to prevent the deformable container from moving when filled with the biological product. In this example, a metallic circular device (304) combined with a reinforcing layer (306) ensures that the deformable container remains hermetic and at the same time ensures the structural integrity of the walls of the deformable container.

The method for freezing biological materials using the system exemplified herein comprises the following steps: placing a collapsible container on the support (100) having at least two overlapped cavities (101) delimited by horizontal heat transfer plates (132) and side walls (103). The deformable container configured to contain biological materials, with an inlet at one end and an outlet at the other end, must be sufficiently long so that it is placed in contact with the heat transfer plates (132) of the support (100), so that the input of the deformable container stays in the top cavity (101) of the support (100) and the outlet in the bottom cavity (101) and the deformable container passes from a cavity (101) to the next by folding the deformable container at the ends of the heat transfer plates. Then, the liquid containing the biological material is introduced within the deformable container so as to fill it partially or totally; the temperature of the heat transfer plates (132) is reduced keeping them below the freezing temperature of the fluid containing the biological materials that is contained in the deformable container.

To fill the deformable container it may be necessary to open the hatch, lower hatch (112) and upper hatch (116) as in the case of this example, since the two doors, main front door (102) and main rear door (104) are well closed with the help of the main door screws (122). The system prepared to receive the biological material to be frozen, has in this case the configuration shown in FIG. 8. The inlet tube (208) and the discharge tube (206) of the deformable container may be accessed through the upper opening (1300) and the lower opening (1302), these openings, upper opening (1300) and lower opening (1302), being able to be closed with the help of two hatches, lower hatch (112) and upper hatch (116). In this case, the deformable container is filled by the introduction of biological material through the inlet tube (208) of the deformable container. Preferably, the deformable container must be filled until the biological material occupies more than 80% of the volume of the cavities (101). The system design ensures that the liquid flows down by gravity during filling of the deformable container, until it reaches the lower part of the lower cavity (101). The deformable container does not slide from the initial position, by the action of fluid flow, because the main front door (102) and the main rear door (104) support it, with help of the guides (1263) of cavity compressible insulator (126) shown in FIG. 4. The guides (1263) maintain the deformable container in place, leaving a side clearance through which fluid may flow. Another way to retain the deformable container in place consists on secure it to support points, which connect the deformable container at the edge of the heat transfer plate (132). As mentioned before, the corresponding points are then attached to each other when the deformable container is assembled on the support (100). In this operation mode, the system uses the embodiment of deformable container shown in FIG. 10. The inlet tube (208) of the deformable container is closed with a clamp (204), and the openings, the upper opening (1300) and lower opening (1302) are closed with two hatches, lower hatch (112) and upper hatch (116), hermetically sealed with the help of screws (125). The air release valves (130) are opened and the system is ready for the freezing process. The freezing begins when introducing a cooled diathermic fluid through the diathermic fluid tube (106). The function of the protection wall (1265) located in the cavity compressible insulator (126) can now be better understood. This protection wall (1265) supports deformable containers with flexible thin walls, preventing said thin wall from being damaged during filling, freezing, and transport. The design of the system allows confining all walls of the deformable container, and thus it is possible to ensure non-rupture during filling, freezing, storage, thawing and discharge. Even very thin wall containers with thicknesses between 50 µm and 250 µm can thus be used with volumes ranging from a few tens to thousands of liters.

An auxiliary unit for temperature control, designated UCT, provides the diathermic fluid, for example silicone oil, under low temperature and a determined flow rate. In the embodiment illustrated in FIG. 5a, when the cavity compressible insulator (126) comprises an electric resistance (1267), this may be activated during the freezing step with sufficient heating power to prevent liquid heat transfer between two consecutive cavities (101). An auxiliary control unit of the electric current supplies the electric current (UCCE), which is connected to the electrical connection (105). The UCCE has a control mechanism that regulates the electric power of each electrical resistance (1267), to ensure that the heat transfer rate between two consecutive cavities (101) is close to zero. The control mechanism may be of negative feedback, by regulating the heating power in order to maintain the temperature of the cavity (101) above the freezing value of the biological material, during the freezing stage. In another control mode, the temporal variation of the heating power is determined a priori, based on a mathematical model of the heat transfer processes involved, as is known to one skilled in the art.

The remaining electrical resistances of the system are not activated during the freezing step. In a particular embodiment of the apparatus, that does not have electric resistances (1267), the UCCE does not activate any electrical resistance during the freezing step. The electric resistances (1267) allow reducing the thickness of the top insulating layer (1262) of cavity compressible insulator (126). The increased complexity of the electrical apparatus, with this particular embodiment, is compensated by reduction of its volume and weight. In the absence of electric resistances (1267), the top insulating layer (1262) must be sufficiently thick to ensure that the temperature at the top of the cavity (101), during the freezing stage, does not fall below the freezing temperature of the liquid product. During the process of freezing, the solution expands as ice begins to grow in the vertical direction. The incremental volume of the frozen solution is absorbed by compressing the top of cavity compressible insulators (126) and the air or gas contained in the consecutive cavities (1264) escapes through the small opening (129) into the channels (142) notched in the internal walls of the main doors. These channels (142) are in contact with the gas orifices (144) and air orifices (164) connecting with the air valves (130). At the end of the freezing phase, the air release valves (130) are closed and the system is ready to be stored in a cold room or chamber. Closing the air release valve (130) allows maintaining the biological materials under hermetic conditions, to minimize transfer of oxygen and water losses, which may occur through by sublimation.

Freezing may be carried out in other operating forms. If the objective is to make freezing the quickly as possible, the temperature of the diathermic fluid is rapidly lowered and a cavity compressible insulator (126) with low thermal resistance and without heating is used. If the objective is to make freezing with unidirectional growth of ice dendrites, one operates with a cavity compressible insulator (126) with high heat resistance or with controlled heating to maintain the top part of the cavity (101) under adiabatic conditions, and one operates with a temperature of the diathermic fluid sufficiently low to cause rapidly ice nucleation at the lower part of the bags of the deformable container. Accordingly it is known that the ice matrix will form from the bottom upwards, having primary dendrites that grow vertically, obtaining at the end of the freezing process a frozen biological material very homogeneous at the macroscopic level and with little cryoconcentration. One may also opt for a freezing mode in which a cavity compressible insulator (126) of high heat resistance is operated or with controlled heating to maintain the upper part of the cavity (101) under adiabatic conditions. The temperature of the diathermic fluid is gradually lowered to allow sub-cooling of the biological material as much as possible. In practice, it is possible to sub-cool the biological material slowly with a lower cooling rate of 1° C. per minute, until the temperature falls between 5 to 25° C. below the freezing temperature. When reaching the predetermined sub-cooling temperature ice nucleation is induced. This nucleation may be caused, for example, by ultrasound, by sudden lowering pressure within cavities (101) or by placing the Peltier plates on the side of the cavities (101). Nucleation occurs rapidly, forming a matrix of primary dendrites that occupy the entire liquid. From this moment on, temperature of the diathermic fluid is lowered even more so to continue freezing of the biological material. At this stage, secondary dendrites that will grow from bottom to top are formed, between the matrixes of primary dendrites. The method for thawing biological materials requires the deformable container, containing the frozen biological materials, assembled on the support (100), where biological materials were frozen. The deformable container has part of its volume distributed through several cavities (101) of the support (100), being said cavities (101) delimited by horizontal heat transfer plates (132) and side walls (103), and another part of the volume of said deformable container is spread out of the cavities (101) of the support (100). The thawing method comprises the following steps: first thawing the biological material portions that are at the outlet of the deformable container using a heater, to allow transfer of the thawed material to another auxiliary container. Next the biological materials portions, that are in the volume of the deformable container, that is outside the cavity (101) of the support (100), are thawed by using a heater, to allow the thawed fraction of materials to flow through the cavities (101) and finally to an auxiliary container; finally the biological material portions, that are in the container volume that is inside the cavities (101) of the support (100), are thawed by heating the heat transfer plates (132), while the thawed biological material portion flows outside the deformable container to a container through the auxiliary discharge tube (206).

This thawing method is performed using, for example, the systems here materialized. For example, in the embodiment that makes use of a cavity compressible insulator (126) and with the deformable container placed inside cavities (101), making a zigzag path, the fluid flows in series from the portion of the deformable container in a cavity (101) to the portion of the deformable container on the side of the cavity (101). In this case, firstly, the diathermic fluid tube (106) is connected to the UCT, and the air release valves (130) are open. Before connecting the UCT, the electrical resistance of the door (150) and the electrical resistance of the support device of the container (1284), which should be sufficiently efficient for a rapid thawing, are activated by UCCE, in order to pre-thaw the biological material portion that is located in the regions wherein the thawed fraction of biological material will flow from a cavity (101) to the next. In the embodiment represented in FIGS. 6 and 7, the electrical resistance of the door (150) and the electrical resistance of the support device of the container (1284) are connected to the electric current through the male connector (152) and female connector (153), which are connected with corresponding connectors located in the casing (124) of the support (100). The male connector (152) and the female connector (153) are connected by electrical connection (105), being the electric current controlled by UCCE. The electrical connection (105) between the corresponding connectors exists while the main front door (102) and the main rear door (104) are closed. After the previous pre-thawing step, the lower hatch (112) is open and the discharge tube (206) of the deformable container is connected to an auxiliary container, after the removal of the clamp (204). The auxiliary recipient may be placed, for example, at an inferior level to the one of the system, so that the thawed fraction of biological material (fluid) flows freely by gravity. Alternatively, the auxiliary recipient can be placed at the same level of the system and use a pump for the liquid to flow as the biological material thaws. Another alternative for forcing the liquid out of the deformable container comprises pressurizing the interior part of the system by introducing a pressurized gas through one of the gas transfer valves. In this example, the lower hatch (112) and the upper hatch (116) must be closed and the discharge tube (206) must pass through an opening (129) placed on the lower hatches (112) and the upper hatch (116) or another part of the casing (124) of the support (100). This opening (129) should be well adjusted to the discharge tube (206) to ensure non-significant losses of pressurizing gas. With the auxiliary recipient connected to the system, the UCT is turned on to circulate hot diathermic fluid through the tube of the diathermic fluid (106). The diathermic fluid temperature should preferably be kept constant during the entire thawing process considering as the maximum temperature value the maximum temperature tolerated by the biological material. The biological material that thaws (fluid) flows through the cavity inside the deformable container to the lower cavity, where it is discharged by the discharge tube (206). With this flow strategy, through preliminary thawing of the product in critical regions of the system, it becomes possible to maintain the frozen fraction of the biological material always in contact with the heat transfer plates (132). In this case, the thawing process occurs very quickly, as the thickness of the liquid layer between the frozen biological material and the plates is reduced to a minimum. This flow strategy also ensures that the full thawing time is very reproducible, since the area of contact between the frozen material and the heating plates remains relatively constant. In case rapid thawing is not desired, the thawing method may also be carried out without the auxiliary recipient.

The thawing method may alternatively be performed using the alternative embodiment of the cavity compressible insulator (126). In this case, the UCCE also connects the electrical resistance of the insulator (402). With this procedure it is ensured that a free path is formed through which the thawed biological material may flow freely, until it reaches the discharge tube (206). The electrical resistance of the support device of the container (1284) is responsible for pre-thawing the material that is inside the discharge tube (206), whereas the electrical resistance of the insulator (402) pre-thaws the biological material laterally, to ensure that the frozen biological material within each cavity (101) is well separated from the side walls (103) and moves freely in the direction of the heated heat transfer plate (1323). The notched edge (404) at the insulator compressible cavity (126) creates free side routes through which thawed material can flow easily, thus contributing to minimize the thickness of the liquid layer between the frozen material interface and the heat transfer plates (132), helping to accelerate the thawing process.

Figure 11:
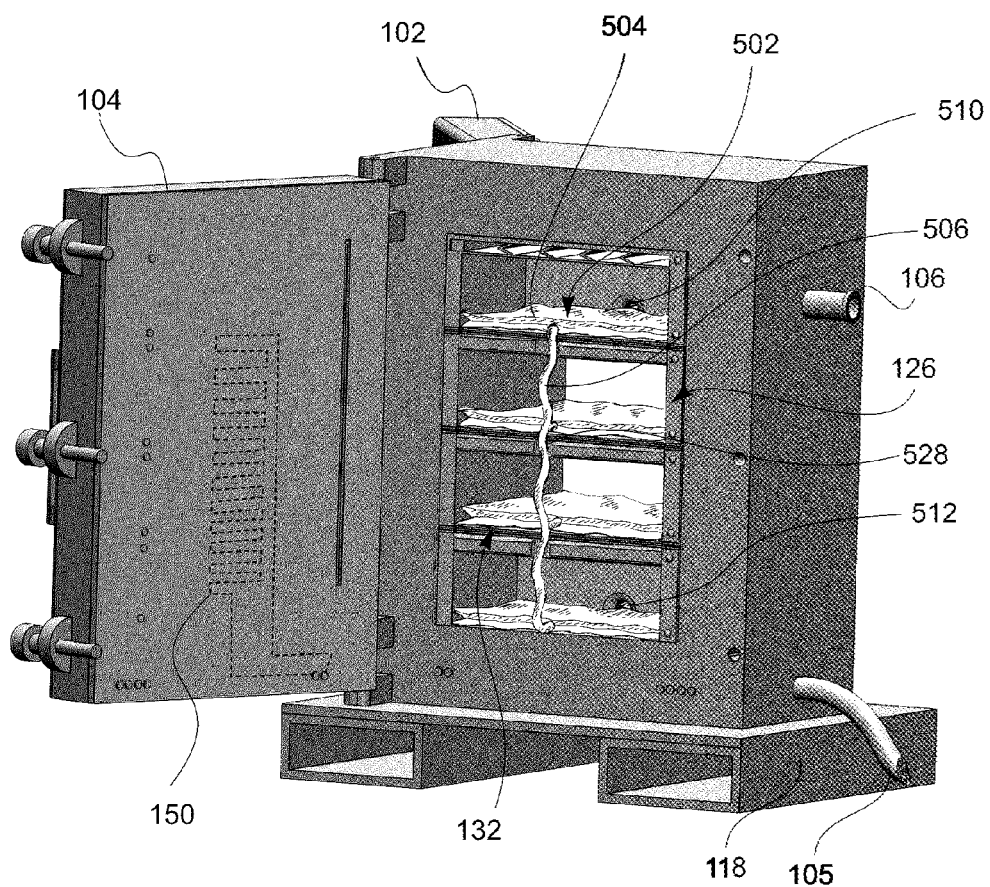
FIG. 11 schematically illustrates a front perspective view of the support, with the two main doors partially open, wherein the reference numerals indicate:
102—main front door.

So far, the described embodiments of the invention always have the deformable container placed in a zigzag pattern in cavities (101). Another way of assembling a deformable container inside the support (100) is done by using a deformable container of multiple bags (502) containing interconnected expandable bags (504) that are in contact with all the heat transfer plates (132). This embodiment of the system is schematically represented in FIG. 11, showing a deformable container of multiple bags (502), with interconnected expandable bags (504) placed in parallel in heat transfer plates (132), which are interconnected to each other by a narrower portion of the container that serves as a flexible interconnection tube (506). In a more generic embodiment of the deformable container of multiple bags (502), the interconnection of multiple expandable bags (504) can be made with one or more channels (142). These channels (142) may have a thicker wall thickness or be reinforced. The feeding tube (510) of the deformable container of multiple bags (502) with interconnected expandable bags (504) passes through the orifice of the support device of the upper container (128) and the posterior outlet tube (512) passes through the orifice of the support device of the lower container (128). In the upper part and lower part of the main rear door (104) hatches are also present, lower hatch (112) and upper hatch (116) to provide access to the feed tube (510) and posterior outlet tube (512). The main front door (102) has an electrical resistance of the door (150) for pre-thaw the product in the interior of the flexible interconnection tube (506), during the thawing step. The cavity compressible insulator (126) is almost identical to that described in the first embodiment, with the difference of presenting a single recess (528) to allow flexible interconnection tube (506) of expandable bags (504) passing from one cavity (101) to the next.

The systems previously described may also include the additional devices presented below, in order to facilitate the process of freezing, storage and thawing of biological material.

Support (100) may optionally have at least one inspection window or hatch made of transparent material, such as glass or polycarbonate, to allow inspection of the biological material, during freezing, thawing or storage. The thickness of the transparent material must be sufficiently high so that no significant heat is transferred through the observation window or hatch. Two or more plates of transparent material may be used to further reduce heat transfer. The inspection windows or hatches should preferably be placed on the doors.

The heat transfer plates (132) may additionally have Peltier plates in order to allow a more precise temperature regulation. The electric control unit controls the electrical current of the Peltier plates.

The height cavities (101) may also be controlled, in an alternative system, by connecting the distributor tubes (136) to flexible inlet and outlet tubes of diathermic fluid. By placing springs or lateral flexible connections between the plates and by applying a hydraulic mechanical compressor in the first or last plate, it is possible to adjust the distance between the heat transfer plates and hence the height cavities (101).

REFERENCES

[1]—BioPharm International, 23(7) (2010) pp. 40-49; Biotechnol Bioeng 2003; 82(6):684-690; J. Pharm. Sci., 102(4) (2013) pp. 1194-1208.
[2]—American Pharmaceutical Review 2011, 14(4) 65-72.

This embodiment is naturally not in any way restricted to the embodiments described in this document and a person of ordinary skills in the area may provide many modification possibilities thereof without departing from the general idea as defined in the claims.

All embodiments above described are obviously combinable with each other. The following claims further define preferred embodiments.

The invention claimed is:
1. A system of preservation, storage and transport of biological materials, the system comprising:
   a support having:
      first and second side walls;
      a front door;
      a plurality of cavities;
      a plurality of compressible insulators, each compressible insulator being disposed in a respective cavity of the plurality of cavities and extending from the first side wall to the second side wall, each compressible insulator comprising a compressible material and being adapted to absorb mechanical stresses caused by expansion of biological materials due to freezing;
      a plurality of heat transfer plates;
      at least one temperature control unit;
      at least one container support disposed in a selected cavity of the plurality of cavities, the at least one container support including an orifice; and at least one deformable container having at least one inlet tube adapted to fit into the orifice of the at least one container support, wherein the at least one deformable container has an outer surface having a surface area greater than 80% of a total surface area of the plurality of cavities and a length and a width that are sufficient to enable the at least one deformable container to be placed within the support in such a manner that the at least one deformable container is in contact with all of the plurality of heat transfer plates.

2. The system of preservation, storage and transport of biological materials according to claim 1, wherein the at least one deformable container is one of a single bag and a plurality of bags.

3. The system of preservation, storage and transport of biological materials according to claim 1, wherein the at least one deformable container has a volume greater than 80% of a total volume of the plurality of cavities.

4. The system of preservation, storage and transport of biological materials according to claim 1, wherein the at least one deformable container has a volume equal to or greater than a total volume of the plurality of cavities when the plurality of cavities are empty.

5. The system of preservation, storage and transport of biological materials according to claim 1, wherein the at least one deformable container comprises a plurality of expandable bags.

6. The system of preservation, storage and transport of biological materials according to claim 1, wherein the at least one deformable container has bellows.

7. The system of preservation, storage and transport of biological materials according to claim 1, wherein the at least one deformable container has a wall made of composite film.

8. The system of preservation, storage and transport of biological materials according to claim 1, wherein the at least one deformable container has fixing elements adapted to connect to the support.

9. The system of preservation, storage and transport of biological materials according to claim 1, wherein each compressible insulator has a front side proximate the front door and extending from the first side wall to the second side wall, a back side opposite and parallel to the front side, and a plurality of internal cavities that are reversibly deformable, the plurality of internal cavities extending from the front side to the back side.

10. The system of preservation, storage and transport of biological materials according to claim 1, wherein the support has at least one opening for gas exchange in the first and second side walls and in the front door.

11. The system of preservation, storage and transport of biological materials according to claim 1, wherein the support has an upper hatch and a lower hatch disposed in one of the side walls and the front door.

12. The system of preservation, storage and transport of biological materials according to claim 11, wherein the upper hatch and the lower hatch are disposed in the front door.

13. The system of preservation, storage and transport of biological materials according to claim 1, wherein each of the heat transfer plates includes a plurality of second cavities adapted to allow circulation of a diathermic fluid.

14. The system of preservation, storage and transport of biological materials according to claim 1, wherein each of the heat transfer plates includes second cavities with static mixers.

15. The system of preservation, storage and transport of biological materials according to claim 1, wherein the support has an electric heating mechanism disposed in an upper portion of each of the cavities.

16. The system of preservation, storage and transport of biological materials according to claim 1, wherein the support has an electric heating mechanism in one or more regions of the front door that contact the at least one deformable container.

17. The system of preservation, storage and transport of biological materials according to claim 1 wherein the front door includes sealants adapted to hermetically seal the cavities.

18. A method of preservation, storage and transport of biological materials comprising the system according to claim 1, the method comprising the following steps for freezing:
   placing in the support the deformable container further having at one discharge tube for passing a liquid containing biological materials from one cavity to the next by folding at the ends of the heat transfer plates;
   introducing the liquid containing the biological materials inside the deformable container so as to fill the deformable container;
   lowering the temperature of the heat transfer plates of the support keeping them below the freezing temperature of the biological materials contained in the deformable container.

19. The method of preservation, storage and transport of biological materials according to claim 18, comprising inserting the compressible material on a top of the plurality of cavities of the support and/or in the first and second side walls.

20. The method of preservation, storage and transport of biological materials according to claim 18, comprising inserting materials for thermal insulation at a top of the plurality of cavities of the support and/or in first and second side walls.

21. The method of preservation, storage and transport of biological materials according to claim 18, comprising introducing or removing gas in the plurality of cavities of the support.

22. The method of preservation, storage and transport of biological materials according to claim 18, further comprising the steps of:
   lowering the temperature of the plates at a speed less than 1° C. per minute until the temperature falls between 5 to 25° C. below the freezing temperature;
   inducing nucleation by, for example, ultrasound, sudden lowering of pressure within the plurality of cavities or by placing Peltier plates on the side of the cavities;
   maintaining the temperature of the plates below the freezing temperature until the biological material becomes completely frozen.

23. A method of preservation, storage and transport of biological materials, comprising the system according to claim 1, the method comprising following steps for thawing:
   thawing the biological materials portions that are in the container outlet by using a heater;
   thawing the biological materials portions that are in the volume of the deformable container that is inside the plurality of cavities of the support by heating the heat transfer plates, while the thawed portion of biological material flows out of the deformable container.

24. The method of preservation, storage and transport of biological materials according to claim 23, comprising introducing a gas for pressurization of the cavities of the support.

25. The method of preservation, storage and transport of biological materials according to claim 23, comprising removing the fluid thawed by means of vacuum.

* * * * *